(12) United States Patent
Burbank et al.

(10) Patent No.: US 6,582,385 B2
(45) Date of Patent: *Jun. 24, 2003

(54) HEMOFILTRATION SYSTEM INCLUDING ULTRAFILTRATE PURIFICATION AND RE-INFUSION SYSTEM

(75) Inventors: Jeffrey H Burbank, Boxford, MA (US); C David Finch, Clinton, MS (US); James M Brugger, Newburyport, MA (US)

(73) Assignee: NStage Medical, Inc., Lawrence, MA (US)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/027,301

(22) Filed: Feb. 19, 1998

(65) Prior Publication Data

US 2001/0041892 A1 Nov. 15, 2001

(51) Int. Cl.[7] .................. A61M 37/00; A61M 1/14; C02F 1/44; B01D 61/00
(52) U.S. Cl. .............. 604/5.04; 210/646; 210/650; 210/652; 210/900; 422/44; 604/6.09
(58) Field of Search ............... 604/4, 5, 6, 317, 604/403, 4.01, 5.01, 6.1, 6.09; 128/898; 210/645–46, 650, 652–53, 651, 638, 641, 648–9, 660, 663, 790, 803–5, 294–95, 321.6, 32.71–321.72, 321.75, 321.84, 433.1, 434, 929, 900; 422/44, 48

(56) References Cited

U.S. PATENT DOCUMENTS

| | | | |
|---|---|---|---|
| 3,579,441 A | | 5/1971 | Brown |
| 3,926,797 A | | 12/1975 | Gigou et al. |
| 4,804,474 A | | 2/1989 | Blum |
| 5,194,157 A | * | 3/1993 | Ghezzi et al. ............. 210/646 |
| 5,352,364 A | * | 10/1994 | Kruger et al. ............. 210/652 |
| 5,484,397 A | | 1/1996 | Twardowski |
| 5,725,776 A | | 3/1998 | Kenley et al. |
| 5,910,252 A | * | 6/1999 | Truitt et al. .................. 210/645 |
| 5,951,863 A | * | 9/1999 | Kruger et al. ......... 210/321.71 |

* cited by examiner

Primary Examiner—Angela D. Sykes
Assistant Examiner—P. M. Bianco
(74) Attorney, Agent, or Firm—Proskauer Rose LLP (57) ABSTRACT

A hemofiltration system is provided in which ultrafiltrate is purified by reverse osmosis for reinfusion. Non-sterile infusate concentrate is dialyzed into the purified ultrafiltrate and combined with cleared blood which is returned to the patient. In another system, a hemofilter is used to sterilize essentially pure, non-sterile water for dilution of sterile infusate concentrate, then the hemofilter is used to filter blood, the infusate concentrate being combined with cleared blood for return to the patient.

3 Claims, 6 Drawing Sheets

HEMOFILTRATION SYSTEM INCLUDING ULTRAFILTRATE PURIFICATION AND RE-INFUSION SYSTEM

FIELD OF THE INVENTION

The present invention relates generally to man-made apparatus that substitutes for natural kidney function, and more particularly to a compact, easy-to-use hemofiltration system in which ultrafiltrate is purified via reverse osmosis to create pure water, and infusate concentrate is combined with the purified ultrafiltrate to create infusate.

BACKGROUND OF THE INVENTION

Loss of human renal function, for example due to kidney disease, affects hundreds of thousands of people worldwide. In the past, chronic renal failure has meant almost certain death. More recently, renal failure is treatable by kidney transplant and/or less-physiologically traumatic procedures such as hemodialysis, hemofiltration or peritoneal dialysis (dialysis therapy). Existing hemodialysis and hemofiltration systems operate by withdrawing blood from a patient, treating the blood to remove waste, and re-introducing treated blood into the patient. Hemodialysis operates by bringing blood into contact with one side of a semipermeable membrane while a dialysis solution (dialysate) is brought into contact with the other side of the membrane. Uremic toxins diffuse out of the blood, through the semipermeable membrane due to a concentration gradient across the membrane, and into the dialysate. Hemofiltration operates by passing the blood through a filter to remove elements smaller than the filter pore size and replacing with a physiologic solution free of toxins (infusate).

The prior art contains examples of blood treatment devices that make use of combinations of multiple dialyzers, multiple filters, or combinations of filter and dialyzer. Kraus, et al., in "Urea-Rejecting Membranes and Their Application in the Development of a Miniature Artificial Kidney", *J Memb. Sci.*, 1, 115–127, 1976 describe a system for continuous regeneration of peritoneal dialysate water. A dialysis unit is provided for purifying peritoneal dialysis solution, and a filter continuously purifying dialysate provided to the dialysis unit.

Ghezzi, et al. (U.S. Pat. No. 5,194,157) describe a blood purification system including, in series, a hemofiltration element followed by a hemodialysis element. Blood from a patient is first filtered in the hemofiltration element, then passed through the hemodialysis element and returned to the bloodstream. Ultrafiltrate from the hemofiltration element can be regenerated by being passed through a second filter and introduced into the flow of blood between the hemofiltration element and the hemodialysis element.

Gigou, et al. (U.S. Pat. No. 3,926,797) describe a separation system that can be used for blood purification. The system includes an ultrafiltration cell that receives blood from a patient, filters the blood, and returns the filtered blood to the patient. The ultrafiltrate can be purified using a dialysis unit, the purified ultrafiltrate combined with filtered blood for re-introduction into the patient. A device such as an active charcoal column or an ion exchange resin column can be used to remove waste from the dialysate of the dialyzer.

Brown (U.S. Pat. No. 3,579,441) described a blood purification unit including an ultrafilter for filtering blood from a patient and returning filtered blood to the patient. The ultrafiltrate can be passed through a hyperfilter, the hyperfiltrate being combined with purified blood for re-introduction into the patient. A reservoir is provided for introduction of make-up electrolyte into the hyperfiltrate for re-combination with the filtered blood. While the above-noted and other systems represent, in many cases, useful contributions to the art, many systems include inherent drawbacks. Hemodialysis, in general, is more expensive, more complex, and more difficult to employ than is hemofiltration. Specifically, where a dialysis unit is used to remove waste from a physiological fluid stream and the stream is being re-introduced into a patient, a relatively large volume of dialysate typically is required to create a continuous passage against the side of the dialyzer semipermeable membrane opposite the side addressed physiological fluid. Since the dialysate must be pure to the extent that it is free of chlorine, fluorine, and other poisonous ions that can cross a semipermeable membrane, significant effort is required to produce the necessary volume of purified water.

In many continuous hemofiltration systems ultrafiltrate waste must be replaced by infusate, which often is provided as a fluid for direct introduction into the patient, for example by being introduced into a conduit returning cleansed blood to a patient. In this instance pure, sterile infusate is required, adding complication and cost.

Most man-made renal function systems are not designed for convenient home use. In general, artificial renal treatment is given in a clinical outpatient setting for reasons of safety, since factors such as fluid balance and equipment complexity are critical. Of course, loss of a threshold amount of blood results in death. However, since victims of renal failure treated by man-made renal function systems must spend a significant amount of time undergoing dialysis therapy, these patients must spend a significant amount of time out of their homes if treated in a clinical setting.

Accordingly, it is a general object of the present invention to provide a blood treatment system which is simple to use that does not requires neither the generation of a large volume of pure dialysate solution, nor provision of a sterile replacement infusate formulation.

SUMMARY OF THE INVENTION

The invention includes, in one aspect, a method of purifying bloodstream waste, for the purpose of replacing kidney function, and in another aspect involves forming an infusate solution suitable for introduction into a patient from sterile or non-sterile infusate concentrates. In another aspect of the invention, a system or systems are provided for performing the above functions.

Specifically, in one aspect of the invention, a method is provided for purifying blood stream waste and forming a forming an infusate. Bloodstream waste from a patient is purified to form essentially pure water. A non-sterile infusate additive is sterilized to form a patient-sterile infusate additive, and the essentially pure water, derived from the patient's blood stream waste, is combined with the patient-sterile additive to form an infusate solution suitable for introduction into the blood stream of the patient.

In some embodiments, the bloodstream waste is purified into essentially pure water by subjecting the bloodstream waste to reverse osmosis to remove uremic toxins, with or without a recycle loop. In another embodiment, the blood stream waste is purified by distillation or exposure to a sorbent. In some embodiments, the bloodstream waste is produced by continuously drawing blood from a patient and subjecting the blood to a purification step, such as hemofiltration, to separate the bloodstream waste from cleansed blood. In other embodiments, the bloodstream waste comprises peritoneal dialysate. In some embodiments of the experiment, the infusate solution is prepared by contacting the essentially pure water, derived from bloodstream waste, with a patient-sterile side of a semi-permeable membrane while simultaneously contacting a nonsterile additive with the opposite side of the membrane, thus allowing the additive to be sterilized while passing through the membrane to form the infusate solution. In certain embodiments of the invention, the infusate solution is combined with the cleansed blood and continuously reinfused into the patient.

Another aspect of the invention involves dialyzing a nonsterile infusate additive into a fluid across a semi-permeable membrane. Net ionic flow across the membrane into the fluid occurs thus creating an infusate solution suitable for introduction into a patient without further treatment.

Yet another aspect involves combining a fluid infusate output from a unit containing a semi-permeable membrane with fluid output from a blood purification device to form an infusate solution suitable for introduction into the bloodstream of a patient. In this aspect of the invention, net ionic flow can occur across the semi-permeable membrane and into the infusate. In some embodiments, a fluid, such as essentially pure water, passes through the semi-permeable membrane unit to form the fluid infusate output and no solutes are removed from the fluid.

The present invention also entails forming essentially pure, sterile water from essentially pure, nonsterile water by passing the nonsterile water through an ultrafiltration membrane. In this embodiment, the resulting essentially pure, sterile water is then added to an infusate concentrate to form an infusate solution. Impure blood is also passed through the ultrafiltration membrane to remove ultrafiltrate waste through the membrane and recover cleansed blood from the membrane.

The invention also includes a method for creating an infusate solution suitable for introduction into a patient by allowing a non-sterile infusate additive to diffuse across a semi-permeable membrane. The membrane separates a container into a non-sterile chamber, within which the infusate additive is contained, and a sterile chamber, containing sterile fluid.

Another aspect involves dialyzing an infusate additive is dialyzed into a fluid stream across a semi-permeable membrane. In this embodiment, a net ionic flow occurs across the semi-permeable membrane into the fluid stream to form an infusate solution which is introduced into the bloodstream of the patient.

The invention also entails passing a fluid stream through a semi-permeable membrane unit. Within the semi-permeable membrane unit, an infusate additive is added to the fluid stream, without removing any solutes from the fluid stream, to form an infusate solution suitable for introduction into a patient.

Another aspect of the invention involves maintaining a concentration gradient across a semi-permeable membrane in a semi-permeable membrane unit. Diffusion then occurs from a first side of the membrane to a second side. The concentration gradient is maintained and diffusion is enabled by feeding fluid with an elevated concentration from a constant volume fluid enclosure to the first side while removing from the first side fluid of a relatively lower concentration. The removed fluid is then returned to the constant volume fluid enclosure.

The invention provides a method of monitoring an infusate solution. The monitoring method involves dialyzing an infusate additive into a fluid stream and measuring the conductivity of the resultant infusate solution.

The invention also provides a method of purifying a solution. The method involves contacting an unpurified fluid stream with a first side of a filter where the stream is divided into two streams. The first stream passes through the filter, and the second stream does not. The second stream is recirculated to the first side of the filter through a recirculation conduit including a receptacle with a variable volume. A portion of the second stream is added to an expandable bag and a constant amount is recirculated to the first side of the filter and added back to the stream of unpurified fluid.

In one aspect of the invention, a method for fluid purification includes establishing a stream of fluid containing a species directed toward a filter having an upstream and a downstream side. A first portion of the stream of fluid passes through the filter free of the species, and a second portion of the fluid, containing the species, is maintained on the upstream side of the filter. The second portion of the stream is diverted from the filter through a recirculation conduit which includes a variable volume receptacle. The second portion of the stream is recirculated and added to the stream of fluid directed toward the filter.

The invention also encompasses various novel apparatus and systems for performing the inventive methods. In one embodiment, a system is provided that includes a semi-permeable membrane unit, which includes a semi-permeable membrane having a patient-sterile and a nonsterile side. The system also includes a water purification unit that has an inlet for receiving impure water and an outlet for delivering purified water. The water purification unit is constructed and arranged to purify the water between the inlet and the outlet. Included also is a fluid conduit that connects the outlet of the water purification unit with the sterile side of the semi-permeable membrane unit. In certain embodiments, the water purification unit comprises a reverse osmosis unit. The system can also include a blood purification unit that receives impure blood from a patient, an separates the impure blood into a cleansed blood stream and a bloodstream waste stream that is deliverable to the water purification unit inlet. In particular embodiments, the blood purification device comprises a hemofilter.

The invention also encompasses systems comprising a semipermeable membrane unit, including a semi-permeable membrane having a patient-sterile side and a nonsterile side where the patient-sterile side is in fluid communication with a patient-sterile conduit that is connectable to a fluid system of the patient. The system also includes fluid circuitry associated with the semi-permeable membrane unit that is constructed and arranged to provide an osmotic pressure driving force that creates net ionic transport across the semi-permeable membrane from the nonsterile side to the patient-sterile side.

One aspect of the invention provides a system including a semi-permeable membrane having a patient-sterile side and a nonsterile side, and a blood purification device having a conduit that is fluidly connectable to the patient's bloodstream for delivering cleared blood to the patient. The system further includes a fluid conduit that allows for connection between the patient-sterile side of the semi-permeable membrane and the fluid conduit of the blood purification device and fluid circuitry associated with the semi-permeable membrane unit that is constructed and arranged to provide osmotic pressure driving net ionic flow across the semi-permeable membrane from the nonsterile to the patient-sterile side.

In another aspect, the system includes a semi-permeable membrane, which has one side in fluid communication with an infusate concentrate, and is fluidly connectable with a bloodstream of a patient without the need to make or break conduit connections.

Another system, as provided by the invention, includes a semi-permeable membrane unit having a semi-permeable membrane with a first side and a second side. The first side is in fluid communication with a conduit that is connectable to a bloodstream of a patient. Also included is fluid circuitry associated with the semi-permeable membrane that is constructed and arranged to provide osmotic pressure to drive ionic transport across the semi-permeable membrane from a nonsterile to a patient sterile side.

Another system of the invention includes a semi-permeable membrane unit with a semi-permeable membrane that has a first side and a second side, the invention provides an enclosure that has an inlet and an outlet, with both the inlet and the outlet being fluidly connectable to the first side of the semi-permeable membrane. The enclosure further includes a movable, nonporous barrier within the enclosure that separates the inlet from the outlet.

Furthermore, the invention also encompasses systems including a semi-permeable membrane unit with a semi-permeable membrane that has a first side and a second side where the first side is surrounded by an enclosure. This enclosure includes an inlet, for receiving fluid for contact with the first side of the membrane, and an outlet for discharging fluid from the first side of the membrane. The inlet and the outlet of the enclosure are in fluid communication with a first and a second sealed fluid container respectively.

Articles are provided by the invention that include a impermeable container separated into two chambers by a semipermeable membrane. The first chamber, bounded on one side by one side of the semi-permeable membrane, is nonsterile. The second chamber, bounded on one side by the other side of the semi-permeable membrane is sterile. In certain embodiments, the chamber can contain a nonsterile infusate additive.

Other advantages, novel features, and objects of the invention will become apparent from the following detailed description of the invention when considered in conjunction with the accompanying drawings, which are schematic and which are not intended to be drawn to scale. In the figures, each identical or nearly identical component that is illustrated in various figures is represented by a single numeral. For purposes of clarity, not every component is labeled in every figure, nor is every component of each embodiment of the invention shown where illustration is not necessary to allow those of ordinary skill in the art to understand the invention.

DETAILED DESCRIPTION OF THE INVENTION

The present invention provides a system for the treatment of blood in patients requiring renal therapy, for example in patients suffering renal failure. The system is constructed to allow hemofiltration and reinfusion without the need for provision of pre-packaged, sterile infusate solution or concentrate. The system also is constructed to be simple to operate safely in the home, and it allows for the possibility of safe and convenient daily hemofiltration treatments. The overall hemofiltration system of the invention includes several inventive components that can be used alone or in combination with other components of the overall system.

Hemofiltration therapy facilitated by the system involves passing blood drawn from a patient through a filter to remove uremic and other blood toxins (waste material that is removed physiologically by a healthy kidney), and subsequent reinfusion of the blood into the patient. An infusate solution, or replacement fluid, is added to the blood returned to the patient to at least in part make up for the amount of fluid removed during the filtration process. Typically, fluid will be replaced in an amount slightly less than that removed to decrease the overall fluid level in the patient.

It is a feature of preferred embodiments of the invention that ultrafiltrate from a hemofiltration device is purified and re-infused into a patient after addition of make-up electrolytes.

A discussion of the state of the art of hemodialysis and hemofiltration systems, and of certain factors and parameters recognized by the inventors of the present invention, will facilitate a better understanding of the implications of the invention. A more detailed discussion can be found in co-pending, commnonly-owned U.S. patent application Ser. No. 08/800,881, entitled "Hemofiltration System", filed Feb. 14, 1997, incorporated herein by reference. Hemodialysis involves establishment of a flow of a patient's blood along a first side of a semipermeable membrane in a first direction, and establishment of a dialysate solution flowing typically in the opposite direction on the opposite side of the membrane. The dialysate has a low concentration (typically zero, initially) of toxins desirably removed from blood, thus a concentration gradient of toxin is established across the semipermeable membrane causing toxins to diffuse across the membrane out of the blood. The process is limited, ultimately, by the rate of diffusion of toxins across the semipermeable membrane, so maintaining a very low concentration of toxins on the dialysate side of the membrane is the most effective means of increasing the blood treatment rate. To do this, however, often requires large quantities of dialysate, typically provided conveniently only in a clinical setting. Many current clinical hemodialysis protocols require approximately 60–120 liters or more of dialysate per treatment, an amount not conveniently delivered. Since dialysates must be free of toxic levels of chlorine and other ions commonly found in tap water, dialysate is perhaps not safely and conveniently prepared by most potential patients.

Since concentration-gradient-driven diffusion of toxins across a membrane is the primary rate limiting factor in dialysis, treatment rate does not increase significantly as blood flow rate adjacent the membrane increases above a certain point. With increasing blood flow rate adjacent a membrane in a dialysis process, treatment rate increases sharply just above zero flow, but quickly tapers off, that is, diminishes in rate of increase until it reaches an approximate plateau in which any increase in blood flow rate results in very little resultant increase in blood treatment rate. The dialysate flow rate could be increased but this requires even more water. In hemofiltration, on the other hand, achievement of acceptably high treatment rates has been determined to be largely dependent upon blood flow rate. Hemofiltration involves convection of toxins across a membrane, specifically, passage of blood through an ultrafiltration membrane that passes toxins but that restricts the passage of blood cells and other components desirably returned to the patient. The toxins are routed to a waste receptacle, and the blood cells and other components trapped by the filter are returned to the patient's bloodstream. Unlike in hemodialysis, in hemofiltration the rate of blood treatment is independent of any concentration gradient across the filter, and instead is dependent upon the rate of clearance of the filter, that is, the rate at which blood cells and other filtrate can be removed from the filter and re-introduced into the patient's bloodstream. The clearance rate is, in turn, dependent only upon the flow rate of the patient's blood through the filter. Therefore, as blood flow rate increases in hemofiltration, toxin clearance rate increases essentially linearly. Moreover, the 60–120 liters of auxiliary fluid, required in hemodialysis (the dialysate), is not required in hemofiltration.

Since repeatable, high blood flow rates have not typically been readily achievable, many prior art hemofiltration techniques have been less efficient than hemodialysis at achievable blood flow rates, therefore leading to hemodialysis being the preferred treatment choice. U.S. patent application Ser. No. 08/800,881, referenced above, commonly-owned, co-pending U.S. provisional patent application Ser. No. 60/036,124 of Burbank, et al., entitled "Valve Port and Method for Vascular Access", filed Jan. 21, 1997, commonly-owned, co-pending U.S. patent application Ser. No. 08/942,990 of Burbank, et al., filed Oct. 2, 1997, entitled "Valve Port and Method for Vascular Access", and co-pending, commonly-owned U.S. patent application Ser. No. 08/724,948, filed Nov. 20, 1996 by Finch, et al., entitled "Subcutaneously-Implanted Cannula and Method for Arterial Access", all incorporated herein by reference, describe apparatus, including a subcutaneously-implanted valve system, that alone or together can facilitate use of a very large-gauge needle, repeatedly, allowing repeated high-flow-rate, high-volume hemofiltration.

With high-flow-rate, high-volume hemofiltration being feasible, there is a need for simple, convenient hemofiltration systems. In hemodialysis a physiologic solution, dialysate, is created which causes a concentration gradient where toxins diffuse out of the bloodstream across a dialysis membrane and make-up electrolytes diffuse into the bloodstream. In hemofiltration, however, an infusate solution, which includes make-up electrolytes, is combined with the filtered blood before it is returned to the patient. The infusate solution must be pure, that is, free of chlorine and other poisonous ions, and must be sterile for introduction into the patient. The present invention provides systems and techniques that facilitate simplified hemofiltration.

Figure 1:
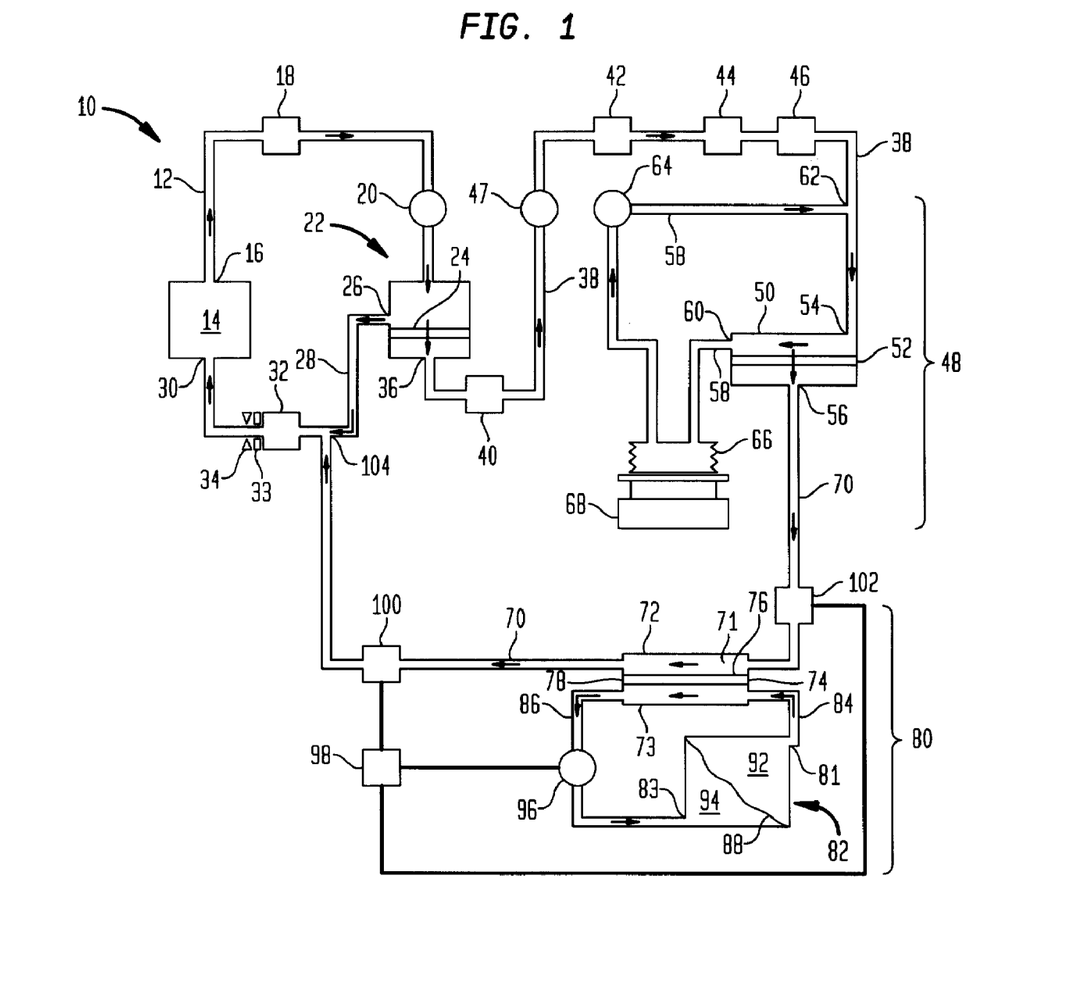
FIG. 1 is a schematic illustration of a hemofiltration system according to one embodiment of the invention in which ultrafiltrate is purified by further filtration, and non-sterile infusate concentrate is dialyzed into the purified ultrafiltrate to create sterilized infusate solution for combination with cleansed blood returned.

FIG. 1 is a schematic illustration of a blood treatment system 10 in accordance with one embodiment of the invention. System 10 facilitates a method for clearing a patient's blood of toxins via hemofiltration, purifying the resulting ultrafiltrate via reverse osmosis to create a purified stream, and combination of the purified stream, following introduction of make-up electrolytes, with the purified blood for re-introduction into the patient. A patient blood withdrawal conduit 12 is connected to the vascular system of a patient 14 at a location 16 which, in preferred embodiments, is a high-flow rate valve port as described in above-referenced application Ser. No. 08/800,881 (Burbank). Patient 14 is a mammal, typically a human. Blood withdrawal conduit 12 passes through an optional pressure detector 18, is routed through a pump 20, and supplies blood to a hemofilter 22. Hemofilter 22 includes an ultrafiltration membrane 24 including pores of size appropriate to retain blood cells and macromolecular species for return to the patient, while passing water, toxins, other waste, and ionic species. Ultrafiltration membrane 24 typically retains species of 1–1000 kDa in size. Treated blood, from which waste has been removed, is retained by ultrafiltration membrane 24 and exits hemofilter 22 upstream of filter 24 at outlet 26 and is delivered, via a conduit 28, to the vascular system of patient 14 preferably by way of a location 30 which, in preferred embodiments, is a high-flow rate port as described above. A drip chamber 32 and a safety clamp 34 preferably are provided along conduit 28. An ultrasonic air detector 33 can be placed after the drip chamber 32 to detect any or all of, flow rate, air bubbles (foam) and hematocrit. Safety clamp 34 can be activated to stop flow if detector 33 indicates the presence of unacceptable levels of air bubbles. The ultrasonic detector and safety clamp can be operably and electronically linked to a treatment controller.

Bloodstream waste (waste ultrafiltrate) exits hemofilter 22 downstream of membrane 24 via exit port 36 and passes through a conduit 38. Conduit 38 can include, optionally, a blood leak detector 40, a pressure detector 42, a carbon filter 44, and/or other system for fluid purification known in the art, for example, an activated charcoal filter or deionization system/ion exchanger 46. A pump 47 maintains waste fluid flow within conduit 38. Downstream of hemofilter 22 waste product is delivered, via conduit 38, to a waste fluid treatment system 48. Waste treatment system 48 includes a reverse osmosis unit (or hyperfilter) 50 including a reverse osmosis (R/O) filter or membrane (hyperfiltration membrane) 52 including pores of a size suitable for passage of essentially pure water and retention of toxins and ionic species including salts. As used herein, "essentially pure water" is meant to define water that, if sterile, could be safely and healthfully infused to a patient. Waste fluid is delivered to reverse osmosis unit 50 via an inlet port 54 at which conduit 38 joins the reverse osmosis unit. An outlet port 56 allows egress of pure water purified by unit 50 from waste fluid delivered from conduit 38.

In a reverse osmosis filtration system such as that illustrated fouling, or clogging, of R/O filter 52 can be problematic. Therefore in some embodiments, the system of the invention includes a recirculation conduit 58 in fluid communication with reverse osmosis unit 50 via a port 60 located upstream of R/O filter 52. Recirculation conduit 58 re-connects with waste fluid conduit 38 at a port 62 upstream of the reverse osmosis unit, creating a recirculation circuit. A pump 64 along conduit 58 drives the recirculation circuit.

An expandable waste receptacle 66 can be provided as part of conduit 58 to facilitate net removal of waste fluid from patient 14. Receptacle 66 can be a bag, an expandable portion of the conduit, or the like, and the net amount of fluid removed from the patient can be controlled by activating an actuator (not shown) associated with the expandable receptacle to control its expansion. A scale 68 can be provided upon which expandable waste receptacle 66 rests for continuous monitoring of the amount of fluid removed.

Downstream of R/O filter 52, essentially pure water exits reverse osmosis unit 50 through port 56 and is carried by an infusate conduit 70 for reinfusion into patient 14. Since essentially all ionic species are removed from ultrafiltrate in waste fluid conduit 38 by reverse osmosis unit 50 (many of which are toxic), make-up ionic species must be added to pure water in infusate conduit 70. While infusate could be directly added to water within conduit 70, the infusate would need to be sterilized first, adding expense and regulatory complication. The invention provides a technique for introduction of ionic species necessary to create a suitable physiological infusate solution from infusate concentrate that need not be pre-sterilized. For this purpose a semipermeable membrane unit 72 is provided along conduit 70 including a semipermeable (ionic) membrane 74. Semipermeable membrane 74 has a side 76 and a side 78 and divides semipermeable membrane unit 72 into a section 71 defined, in part, by side 76 and a section 73 defined, in part, by side 78. Side 76 is in contact with fluid flowing through conduit 70, and section 71 defines a portion of conduit 70 at semipermeable membrane unit 72. Side 76 and section 71 of semipermeable membrane 74 are patient-sterile. "Patient-sterile", as used herein, defines a condition in which a surface of an article is sterile or is a sterile surface having been contacted by physiological fluid of a particular patient only. Side 78 of semipermeable membrane 74 and section 73 of the semipermeable membrane unit, opposite side 76 of the membrane and section 71 of the unit, need not be sterile.

According to one set of embodiments an infusate system 80, including semipermeable membrane unit 72, includes a fixed-volume fluid pathway defined in part by section 73 of semipermeable membrane unit 72. The fixed-volume pathway defines fluid circuitry associated with the semipermeable membrane unit 72 constructed to maintain a concentration gradient across semipermeable membrane 74 to provide net ionic transport from section 73 of unit 72 into section 71. The circuitry includes a fixed-volume container 82, a conduit 84 connecting an outlet 81 of container 82 with an upstream portion of section 73 of membrane 74, and a conduit 86 connecting a downstream portion of section 73 with an inlet 83 of container 82. Container 82 contains a flexible, impermeable wall 88, made of polyvinyl chloride (PVC) or the like, separating container 82 into an upstream section 92 in fluid communication with outlet 81 and a downstream section 94 in fluid communication with inlet 83. A pump 96 is provided along conduit 86 for urging fluid out of non-sterile section 73 of semipermeable membrane unit 72, through conduit 86 and inlet 83 into downstream section 94 of fixed-volume container 82, and urging fluid from upstream section 92 of the container through outlet 81, conduit 84, and into non-sterile section 73 of the semipermeable membrane unit. A controller 98, operably linked to a conductivity cell 100 along infusate conduit 70 downstream of semipermeable membrane unit 72, and optionally to a conductivity cell 102 upstream of unit 72, controls the speed of actuation of pump 96.

Infusate conduit 70 connects, at a port 104, with blood return conduit 28.

The following description of operation of the system of FIG. 1 describes continuous operation. However, it is to be understood that batch processes also are embraced by the invention. For example, a batch sample of uremic toxin containing blood can be treated using the system described with reference to FIG. 1 to provide cleansed blood for infusion into a patient. In addition, separate components and combinations of components of FIG. 1 can be used together in a variety of combinations to provide batch treatment of uremic toxin containing blood or peritoneal dialysate, or batch production of infusates from pure, sterile water and a nonsterile infusate additive. Separate uses of separate components and combinations of components are described below primarily in connection with the continuous operation, but these units can be used in batch systems as well.

In continuous (online) operation, uremic-toxin containing blood is withdrawn from patient 14 via conduit 12 driven by pump 20 and introduced into hemofilter 22. Pump 20 creates a pressure on the upstream side of ultrafiltration membrane 24, driving toxin-containing aqueous ultrafiltrate through the membrane and into waste fluid conduit 38. Waste fluid is delivered by conduit 38 to reverse osmosis unit 50 where, due to a pressure on the upstream side of R/O filter 52 created by pump 47, a first portion of the stream of ultrafiltrate is driven through filter 52 and into infusate conduit 70. Uremic toxins and ions are retained upstream of filter 52 in a second portion of the stream of bloodstream waste, which is diverted from the filter and recirculated through recirculation conduit 58 and expandable receptacle 66 and driven by pump 64 for reintroduction into conduit 38 at port 62. The recirculation circuit facilitates a high rate of fluid flow against the upstream side of R/O filter 52, minimizing clogging and fouling. For example, waste fluid can be delivered from conduit 38 at a rate of 100 ml/min, fluid can flow within recirculation conduit 58 at a rate of 400 ml/min, and pure water can be driven through filter 52 at a rate at 100 ml/min.

Expandable receptacle 66 can be expanded controllably to remove net fluid from the patient. Expandable receptacle 66 can be provided at other suitable locations in the overall system as well, for example along conduit 38.

Essentially pure water is carried from reverse osmosis unit 50, via infusate conduit 70, to semipermeable membrane unit 72 where replacement ionic species are introduced to create an infusate solution for recombination with cleansed blood, delivered by blood return conduit 28, at port 104. This technique involves adding infusate to a fluid stream to form a physiologic solution without removing solutes from the fluid stream, as is effected using traditional dialysis.

A concentration gradient is created across membrane 74 of semipermeable membrane unit 72 that drives net ionic flow into infusate conduit 70 as follows. Infusate concentrate is provided in upstream section 92 of fixed volume container 82. Initially, impermeable, flexible wall 88 is positioned such that upstream section 92 essentially completely dominates fixed volume container 82 and downstream section 94 has a volume which is essentially zero. As pure water flows through patient-sterile section 71 of the semipermeable membrane unit, ions flow across membrane 74 into section 71 since infusate concentrate is positioned on non-sterile side 73. The ionic concentration in conduit 70 downstream of semipermeable membrane unit 72 is maintained within a desired range through use of a conductivity cell 100 providing input to a controller 98 which controls pump 96. The ionic concentration in conduit 70 downstream of semipermeable membrane unit 72 is maintained within a desired range as follows. As ions flow across membrane 74, they are removed from the fluid in non-sterile section 73 and added to the fluid in sterile section 71. The rate of transport of ionic species across membrane 74 and the ionic concentration in conduit 70 downstream of semipermeable membrane unit 72 depends upon the concentration gradient of ionic species across membrane 74, which, in turn, depends on the relative supply rate of fluids to the sterile 71 and non-sterile 73 sections of semipermeable membrane unit 72. For a given flow of sterile infusate in conduit 70, the concentration gradient established across membrane 74 and the ionic concentration detected by conductivity cell 100 will be related to the supply rate of non-sterile infusate concentrate. When conductivity cell 100 detects an ionic concentration which is outside a desired range controller 98 can actuate, deactuate or change the pumping rate of pump 96 until the ionic concentration detected by conductivity cell 100 is within range. For example, if the ionic concentration detected by conductivity cell 100 falls below a desired range, conductivity cell 100 detects this drop and controller 98 actuates or increases the pumping rate of pump 96 which withdraws ion-depleted fluid from non-sterile section 73 and urges it into downstream portion 94 of fixed-volume container 82 which, in turn, via wall 88, urges infusate concentrate from upstream portion 92 via conduit 82 into non-sterile section 73, thus increasing the ionic concentration in non-sterile section 73 and the concentration gradient across membrane 74. During continuous operation, pump 96 operates continuously at a very slow rate and, during the course of an entire treatment protocol, upstream side 92 of container 82 is nearly depleted while downstream side 94 expands to receive depleted fluid (essentially water).

Various sections of system 10 can be used in combination with other components including some not shown, or alone. For example, infusate system 80 can be used in combination with essentially any blood purification apparatus to create an infusate solution from a non-sterile infusate concentrate or separate concentrates. In such a situation, waste product purification system 48 can be used, or can be absent, so long as system 80 is supplied with pure, sterile water. Suitable systems for obtaining pure, sterile water other than waste product purification system 48 can include distillation, sorbent, dialysis, and other purification techniques. In another embodiment, hemofilter 22 can be any blood purification system that removes toxin-containing water and returns cleared blood to a patient. Such an arrangement is defined by blood purification device 22, conduit 28 fluidly connectable to the patient's bloodstream for delivering cleared blood, and conduit 70 connecting the sterile side 76 of semipermeable membrane unit 72 and fluid conduit 28.

Fluid circuitry is provided in system 80 that is constructed and arranged to provide osmotic pressure driving ionic transport across semipermeable membrane 74 from the non-sterile side 78 to the sterile side 76. In this way, fluid infusate output from semipermeable membrane unit 72 is combined with fluid output from blood purification device 22 to provide a physiologic solution suitable for introduction into the bloodstream of patient 14.

Another combination of components that is useful in a variety of settings includes waste fluid purification system 48 in combination with infusate system 80. This arrangement involves an inlet 54 for receiving impure water and an outlet 56 for delivering pure water, the water being purified by a filter 52 located between the inlet and the outlet. Fluid conduit 70 connects the outlet of the purification unit with patient-sterile side 76 of semipermeable membrane 74 of semipermeable membrane unit 72. This arrangement can be used to purify bloodstream waste to form pure water, and to provide a patient-sterile infusate additive from a non-sterile infusate additive by purifying the additive by passage across membrane 74. The pure water and patient-sterile infusate additive are combined to form a physiologic solution suitable for introduction into the bloodstream of patient 14. A continuous process, similar to that illustrated in FIG. 1 can be carried out, or a batch process can involve collecting a batch of bloodstream waste from a patient, purifying the waste to form essentially pure water, and creating infusate solution by dialyzing initially non-sterile infusate additives into the essentially pure water.

One particularly useful application utilizing waste product purification system 48 and infusate system 80 involves treatment and reprocessing of peritoneal dialysate for reuse in a patient. In this application, uremic toxin-containing peritoneal dialysate is collected from the patient into a suitable container and comprises the input solution to filter unit 52. The essentially pure water thus formed is reconstituted with one or more additives (such as ions) through use of infusate system 80. The suitably reconstituted solution is then collected from conduit 70 for reinfusion into the patient's peritoneum for a subsequent dialysis.

Infusate system 80, or a similar system embraced by the invention, can be used in a variety of batch or continuous techniques to dialyze non-sterile infusion additives into a fluid to form a physiologic solution suitable for introduction into a patient without further treatment. "Suitable for introduction into a patient without further treatment", in this context, would be understood by those of ordinary skill in the art to mean free of poisonous molecular or ionic species to the extent that a patient is not poisoned, and free of uremic toxins or containing a low enough concentration of uremic toxins that the fluid is useful within a patient for withdrawal of uremic toxins. For example, bulk amounts of pure, sterile water can be provided, and non-sterile infusate concentrate can be selectively dialyzed into the pure sterile water for infusion for a variety of treatment protocols. This technique avoids the necessity of creating, storing, and shipping a separate, diluted, sterile infusate for all of a wide variety of separate therapeutic agents. Instead, containers of pure, sterile water (or saline), can be stored and shipped and, into each container, any of a wide variety of non-sterile therapeutic agents can be dialyzed before or during infusion. As is apparent, significant regulatory complication is avoided in this technique. The constant-volume container 82 of system 80 also can be used in a wide variety of techniques not limited to the system of FIG. 1.

Similarly, the detection and control system including conductivity cell 100, controller 98, pump 96, and optional conductivity cell 102, can be used in systems not limited to the system of FIG. 1.

One advantage of use of the overall system of FIG. 1, in which ultrafiltrate from hemofilter 22 is processed at system 48 into essentially pure, patient-sterile water for infusion, is that the system is constructed to deal with known contaminants since it is a cyclical process, versus water sources in traditional processes in which there typically is high variability in the level and identity of contaminants.

Figure 2:
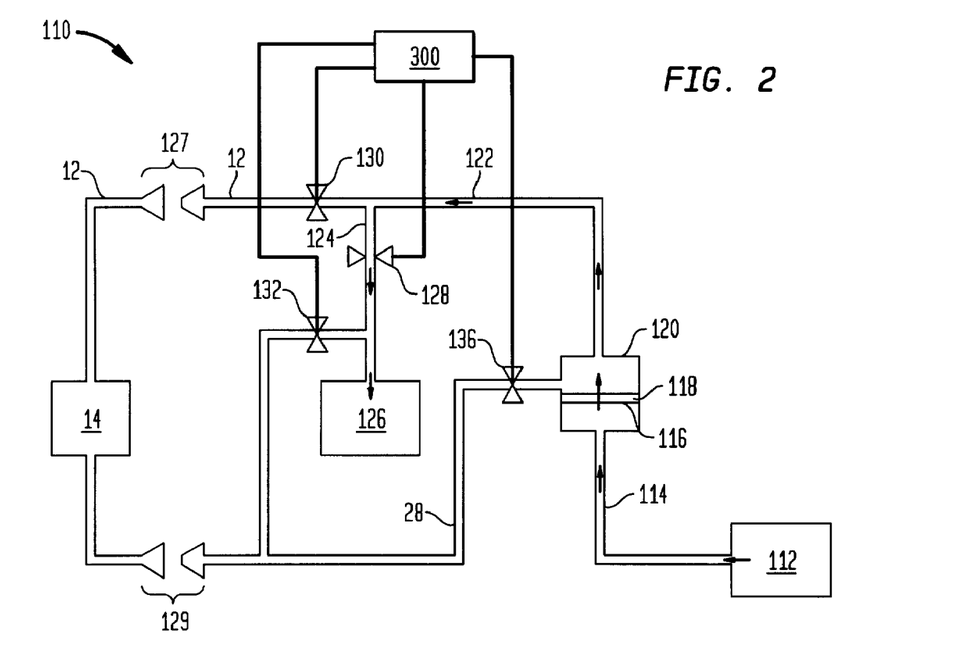
FIG. 2 is a schematic illustration of a hemofiltration system according to another embodiment of the invention in which a hemofilter is used to sterilize pure, non-sterile water for formation of an infusate solution.

Referring now to FIG. 2, a system 110 is illustrated schematically in which a hemofiltration unit can be used both to sterilize water for creation of infusate, and for traditional hemofiltration. System 110 can include pumps, blood leak detectors, pressure detectors, carbon filters, drip chambers, and the like as would be recognized by those of ordinary skill in the art, but these components have been removed for clarity. FIG. 2 illustrates a first cycle of a two-cycle hemofiltration system. In FIG. 2, a container 112 contains essentially pure, non-sterile water that is fed, via a conduit 114, to a non-sterile side 116 of an ultrafiltration membrane 118 of a hemofilter 120. Water crosses membrane 118 and is thereby sterilized, and the resulting essentially pure, sterile water is fed, via a conduit 122 and a conduit 124, to a container 126 containing sterile infusate concentrate. Water sterilized at hemofilter 120 dilutes infusate concentrate in container 126 creating an infusate solution. During the fist cycle, illustrated in FIG. 2, the system is typically not connected to patient 14, as illustrated by separation at un-coupled connections 127 and 129.

Figure 3:
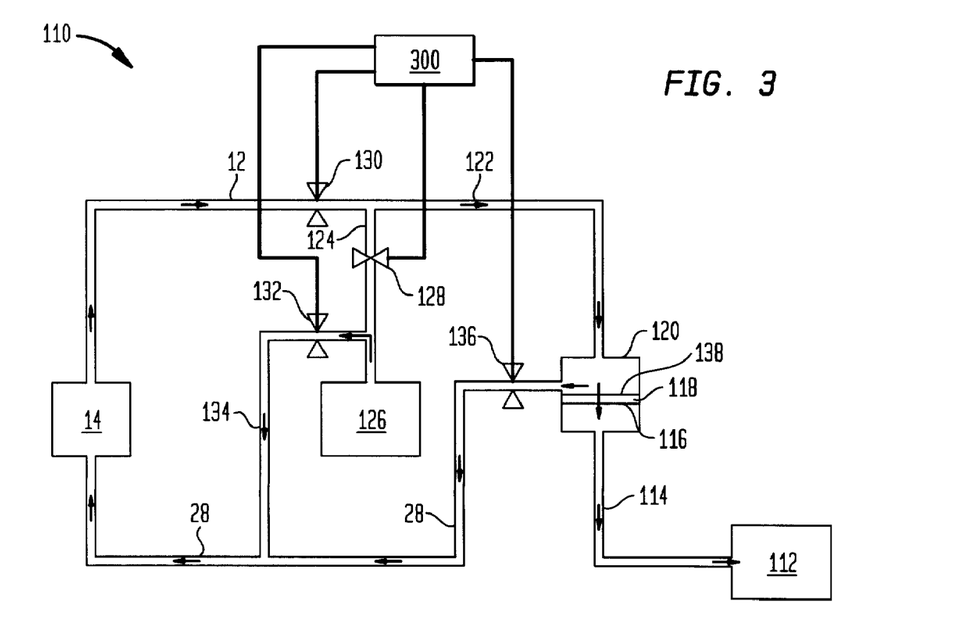
FIG. 3 is a schematic illustration of the hemofiltration system of FIG. 2 in which cleansed blood, after hemofiltration, is combined with infusate solution created from water that has been sterilized using the hemofilter.

Referring to FIG. 3, in a second cycle, subsequent to creation of infusate solution in container 126 (FIG. 2), a valve 128 along conduit 124 is closed, and a valve 130 is opened connecting blood withdrawal conduit 12 with conduit 122, a valve 132 is opened connecting container 126 with an infusate conduit 134 for communicating with cleared blood return conduit 28, and a valve 136 is opened fluidly connecting upstream, sterile side 138 of ultrafiltration membrane 118 with blood return conduit 28. In this second cycle impure blood, containing uremic toxins, is withdrawn from patient 14 through conduit 12, is passed through hemofilter 120, and cleared blood is returned through return conduit 28 and combined with infusate supplied from container 126 via conduit 134 to form a combination introduced into the blood stream of patient 14. Waste from hemofilter 120 is passed through conduit 114 and deposited in container 112.

The system of FIGS. 2 and 3 need not include all of the specific connections, valves, and fluid pathways illustrated. As would be apparent to those of ordinary skill in the art, given the benefit of the disclosure of this application, a variety of simplified connections can be made while maintaining the principle of operation illustrated in FIGS. 2 and 3.

The system of FIGS. 2 and 3 can define a very simple, compact and disposable or reusable unit for home use. One advantage of the system of FIGS. 2 and 3 is that two separate uses of a single membrane 118 reduces costs associated with the system and methods for use of the system. The system includes an ultrafiltration membrane, one side of which is in fluid communication with an infusate concentrate in container 126, and is connectable fluidly with the bloodstream of patient 14 via conduits 12 and 122 without making or breaking conduit connections. That is, valves simply need to be opened and closed, and no fluid connections need to be disassembled and reconnected. This provides significant simplicity for home use. An automatic processor 300 controls required opening and closing of valves and operation of pumps (not shown) to quickly and easily create infusate solution from non-sterile water, and then re-adjust valves and pumps to conduct hemofiltration using the infusate so created.

Figure 4:
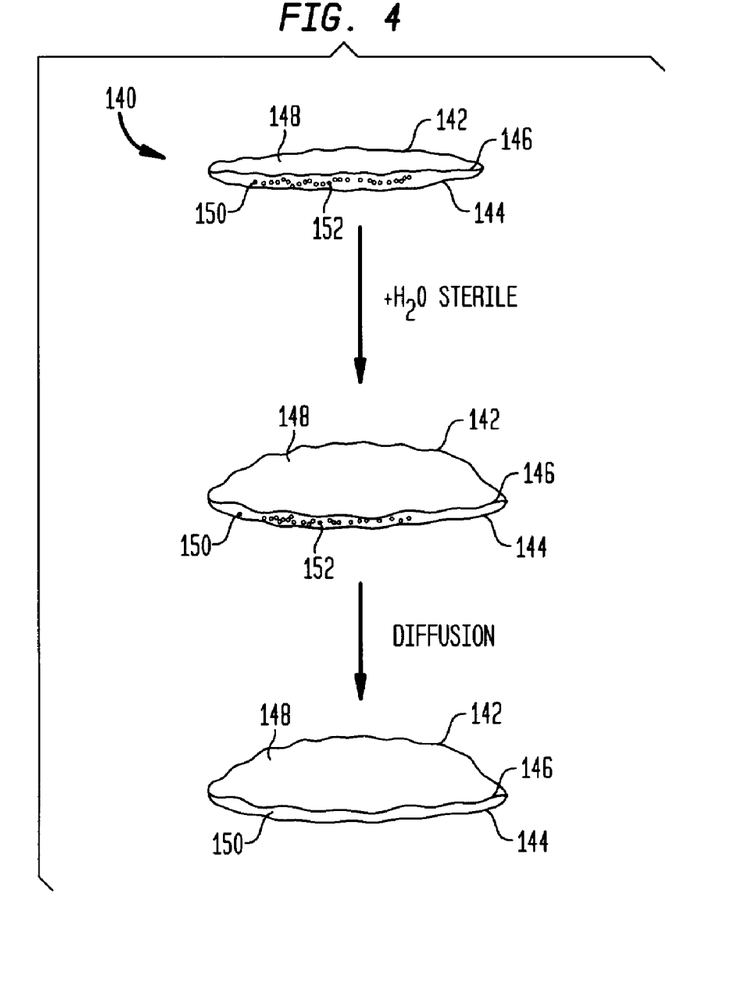
FIG. 4 is a schematic illustration of a container, for use in blood treatment, for creation of a sterile infusate solution from a non-sterile infusate concentrate.
Figure 9:
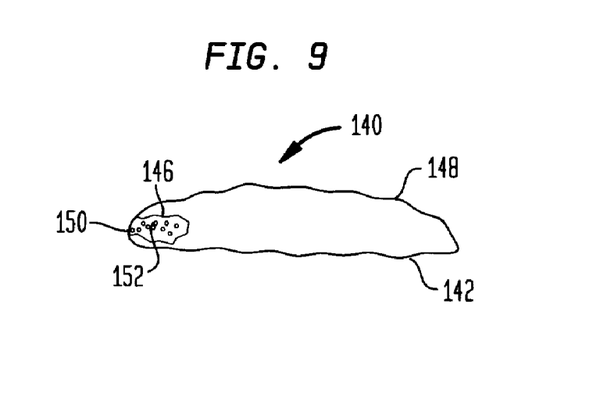
FIG. 9 is a schematic illustration of another embodiment of a container, for use in blood treatment, for creation of a sterile infusate solution from a non-sterile infusate concentrate.

The present invention also provides techniques for formation of a sterile infusate solution from a non-sterile infusate concentrate without the use of pumps or other driven apparatus. Referring to FIG. 4, a container 140 is provided that is defined by a first flexible, non-porous wall 142 and a second flexible, non-porous wall 144, each made of PVC or the like, separated by a flexible, semipermeable membrane 146 for transport of ionic species. A chamber 148 is created between wall 142 and membrane 146, and a chamber 150 is created between membrane 146 and wall 144. Wall 144 and flexible, semipermeable membrane 146 are fastened to each other at several locations such that they can not become physically separated from each other. All interior surfaces defining chamber 148 are sterile or patient-sterile while surfaces defining the interior of chamber 150 need not be sterile. A non-sterile infusate concentrate 152 is provided in chamber 150. Sterile water is added to chamber 148 via a port (not shown) and, after a period of time, the infusate concentrate will diffuse across semipermeable membrane 146, creating in chamber 148 a sterile infusate solution. An alternative embodiment of container 140 is shown in FIG. 9, as viewed from the same direction as in FIG. 4. In this alternative embodiment, chamber 150 comprises a small bag or pouch contained at least partially within chamber 148. In preferred embodiments, the internal volume of chamber 150 is small compared to the internal volume of chamber 148. Chamber 150 is surrounded, at least in part, by a semipermeable membrane 146. In preferred embodiments, chamber 150 is attached to the inside surface of non-porous wall 142 at at least one point of attachment.

Figure 5:
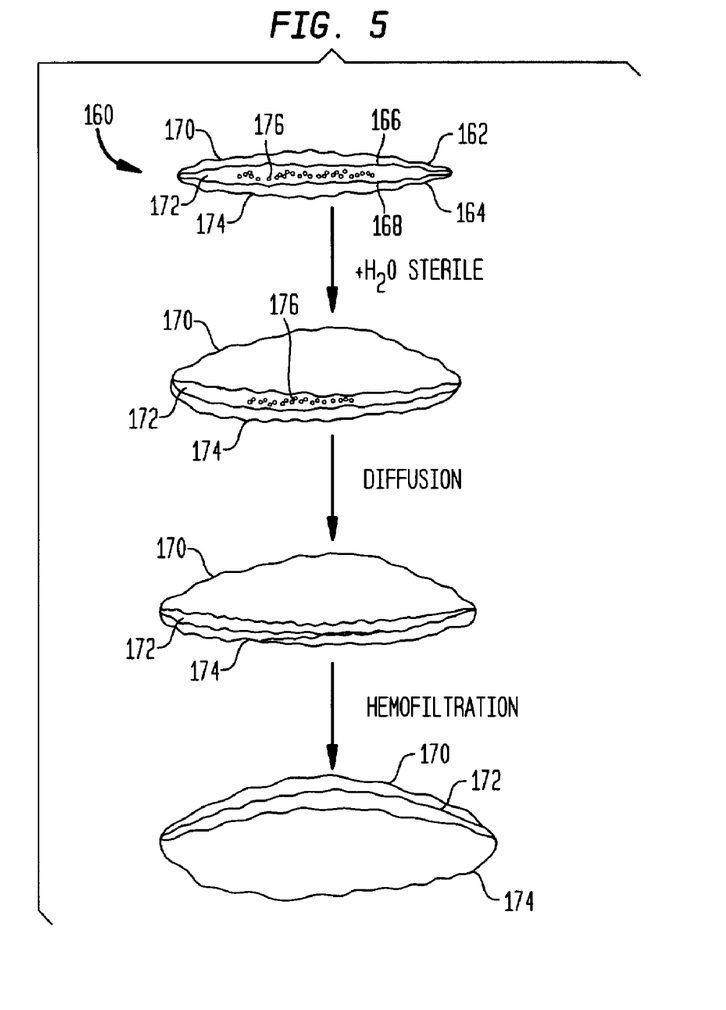
FIG. 5 is a schematic illustration of a container, for blood treatment, for creation of sterile infusate solution from a non-sterile infusate concentrate and for storage of ultrafiltrate replaced by infusate.
Figure 10:
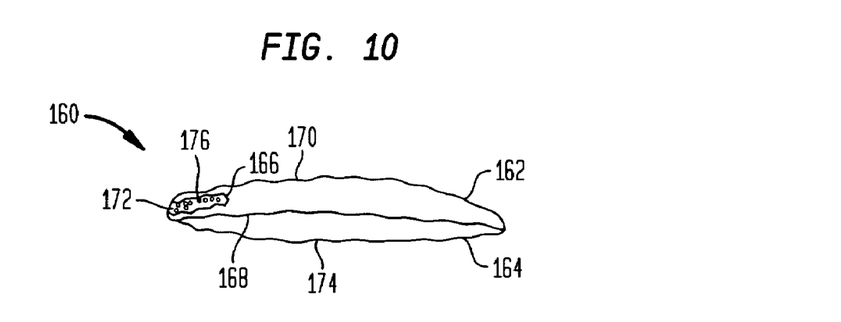
FIG. 10 is a schematic illustration of alternate embodiment of the container of FIG. 5.

Illustrated in FIG. 5 is another embodiment in which a container 160 is defined by outer PVC walls (or other non-porous walls) 162 and 164, a semipermeable membrane 166 provided therebetween, and another PVC wall 168 provided between membrane 166 and wall 164. Semipermeable membrane 166 and PVC wall 168 are fastened to each other at several locations so that they can not become physically separated from each other. Three chambers 170, 172, and 174 are thereby defined by wall 162 and membrane 166, membrane 166 and wall 168, and wall 168 and wall 164, respectively. Interior surfaces of chamber 170 are sterile or patient-sterile, while interior surfaces of chambers 172 and 174 need not be sterile. A non-sterile infusate concentrate 176 is provided in chamber 172. Addition of sterile water to chamber 170 via a port (not shown), followed by diffusion of concentrate from chamber 172 into chamber 170 results in creation, in chamber 170, of sterile infusate solution. Infusate solution can be withdrawn from chamber 170 in a hemofiltration protocol, and ultrafiltrate waste from hemofiltration can be introduced into chamber 174 during hemofiltration. Container 160 thus serves both to create sterile infusate solution from non-sterile concentrate for hemofiltration, and to collect waste from the hemofiltration process. An alternative embodiment of container 160 is shown in FIG. 10, as viewed from the same direction as in FIG. 5. In this alternative embodiment, chamber 172 comprises a small bag or pouch contained at least partially within chamber 170. In preferred embodiments, the internal volume of chamber 172 is small compared to the internal volume of chamber 170. Chamber 172 is surrounded, at least in part, by a semi-permeable membrane 166. In preferred embodiments, chamber 172 is attached to an inside surface of non-porous wall 162 and/or wall 168 at at least one point of attachment.

Figure 6:
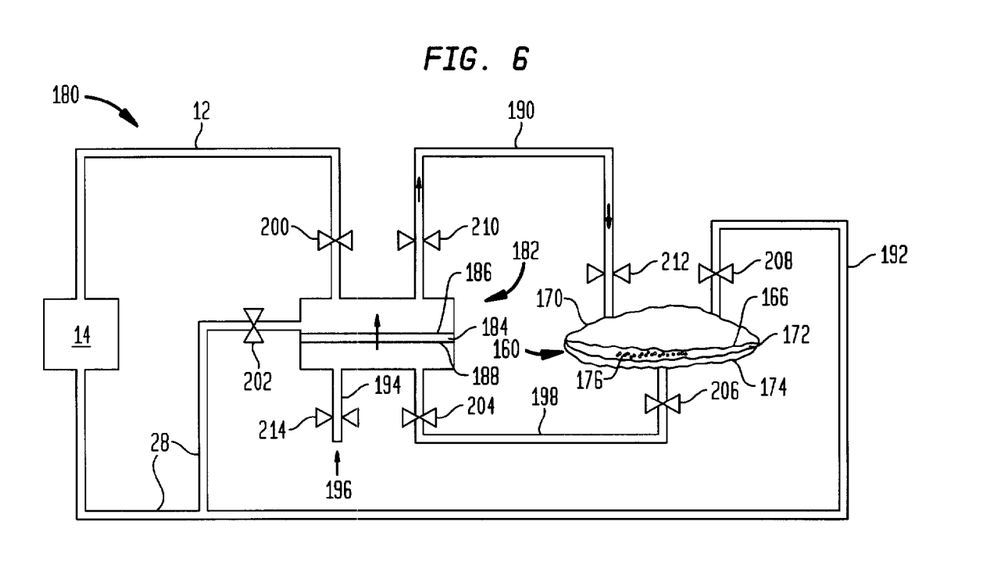
FIG. 6 is a schematic illustration of a hemofiltration system according to another embodiment of the invention utilizing the container of FIG. 5.
Figure 7:
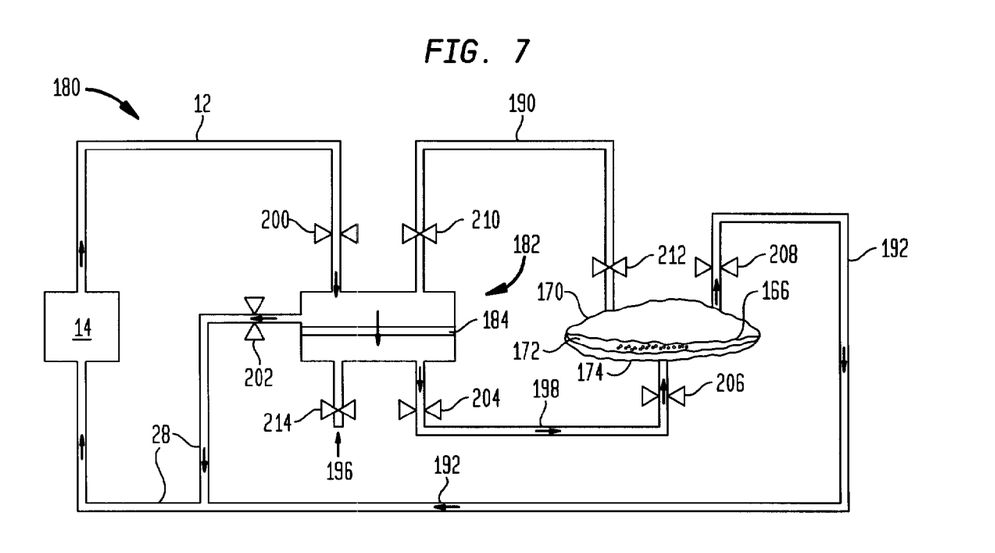
FIG. 7 is a schematic illustration of the hemofiltration system of FIG. 6 following creation of sterile infusate solution from non-sterile concentrate.
Figure 8:
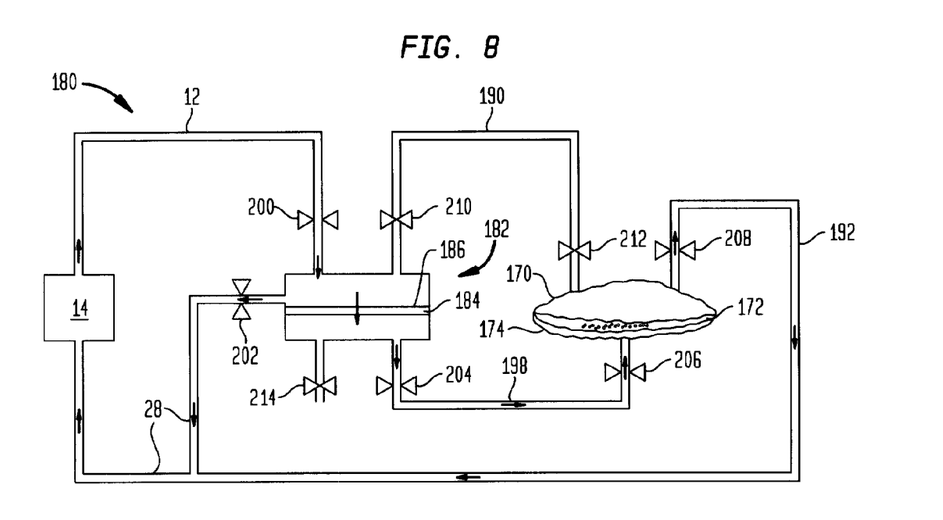
FIG. 8 is a schematic illustration of the hemofiltration system of FIGS. 6 and 7 near the end of a treatment protocol.

Referring to FIGS. 6–8, a hemofiltration system 180 is provided that makes use of container 160 illustrated in FIGS. 5 or 10. System 180 includes a hemofilter 182 including an ultrafiltration membrane 184 having a patient-sterile side 186 and a non-sterile side 188. Sterile side 186 is connected, via blood withdrawal conduit 12, to a patient 14 and also, via a return blood conduit 28, to patient 14. Sterile side 186 of filter membrane 184 also is connected, via a conduit 190, to chamber 170 of container 160, which chamber 170 also is connected via infusate conduit 192 to blood return conduit 28. Non-sterile side 188 of ultrafiltration membrane 184 is connected, via a conduit 194, to a source 196 of pure, non-sterile water and via a conduit 198 to chamber 174 of container 160. Infusate concentrate 176 is provided in chamber 172 of container 160. System 180 can also include pumps, blood leak detectors, pressure detectors, carbon filters, drip chambers, and the like as would be recognized by those of ordinary skill in the art, but those components have been removed for clarity.

In a first cycle of system 180 valves 200 and 202, connecting the sterile side of the ultrafiltration membrane to conduits 12 and 28, respectively, are closed, as are valves 204 and 206, connecting conduit 198 with the non-sterile side of the ultrafiltration membrane and with chamber 174 of container 160, respectively, and valve 208 connecting chamber 170 of the container with infusate conduit 192. Pure, non-sterile water is delivered from source 196, via conduit 194, to the non-sterile side of hemofilter 182, passes across ultrafiltration membrane 184 and is thereby sterilized, and passes through conduit 190 into chamber 170 of container 160. Pumps and processors driving the cycles are not illustrated. Once chamber 170 is full (FIG. 7) valves 210 and 212, connecting conduit 190 to the sterile side of the ultrafiltration membrane and container 170, respectively, are closed, as is valve 214 connecting the source of water to the non-sterile side of the membrane. Infusate concentrate diffuses across semipermeable membrane 166, creating infusate solution in chamber 170. When hemofiltration is desired, valves 200, 202, 204, 206, and 208 are opened, blood is withdrawn from patient 14, via conduit 12, into hemofilter 182 where toxin-containing fluid is withdrawn across ultrafiltration membrane 184, through conduit 198, and into chamber 174 of container 160 (FIG. 8). Cleared blood is returned from the upstream, sterile side 186 of ultrafiltration membrane 184 through conduit 28 and returned to patient 14. Infusate solution is provided, from chamber 170, via conduit 192, to be combined with cleared blood in conduit 28 to form a combination for infusion into patient 14.

Figure 11:
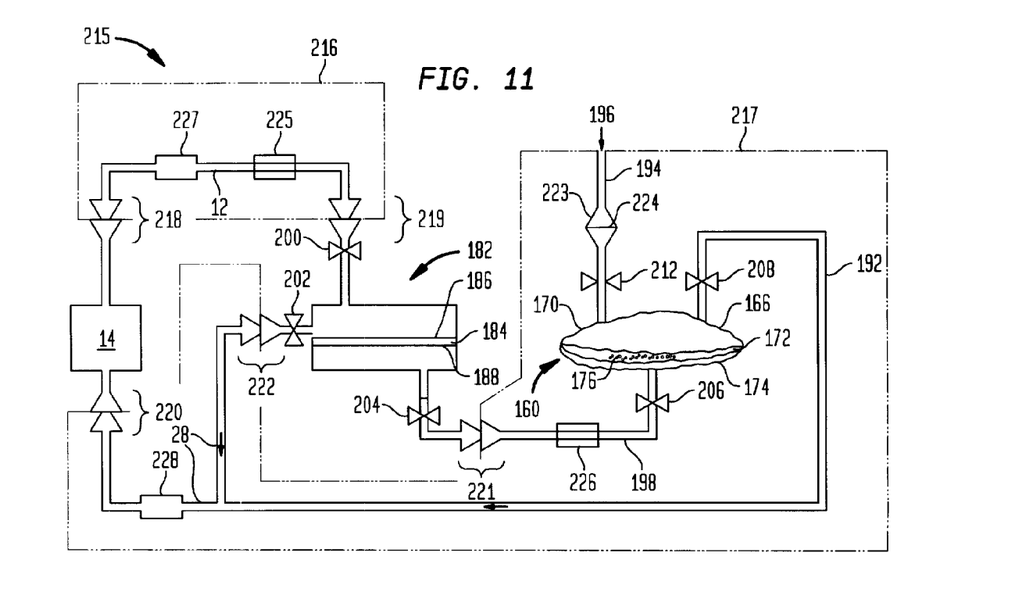
FIG. 11 is a schematic illustration of a hemofiltration system according to another embodiment of the invention utilizing the container of FIG. 5.

An alternative embodiment for the hemofiltration system 180 described in FIGS. 6–8 is presented in FIG. 11. Hemofiltration system 215 in FIG. 11 makes use of container 160 illustrated in FIGS. 5 or 10 and is analogous to hemofiltration system 180 with the following modifications. Unlike hemofiltration system 180 where the hemofilter 182 was used both during the first cycle to sterilize pure, non-sterile water and subsequently for hemofiltration of blood, in alternative embodiment hemofiltration system 215, hemofilter 182 is only used for hemofiltration of blood, and a separate filter unit 223 is provided which is dedicated to the sterilization of pure, non-sterile water from source 196. According, unlike the hemofilter in the embodiments previously described and shown in FIGS. 6–8, hemofilter 182 in FIG. 11 does not require connection to chamber 170 of container 160 or connection to a source of pure, non-sterile water.

The operation of hemofiltration system 215 is similar to that of hemofiltration system 180 previously described. In particular, in the first cycle, when utilizing system 215, pure, non-sterile water is delivered from source 196, via conduit 194 to filter unit 223, passes across sterilizing filter 224 and is, thereby, sterilized before entering chamber 170 of container 160. Pumps and processors driving the cycles are not illustrated. Once chamber 170 is full (not shown) valve 212 would be closed, infusate concentrate 176 would diffuse across semipermeable membrane 166 creating infusate solution in chamber 170. A subsequent hemofiltration cycle would then proceed in the same manner as previously outlined for hemofiltration system 180 (FIGS. 7 and 8).

Certain of the components of hemofiltration system 215 may be conveniently provided in the form of a disposable kit for use with a single patient. The components of such a kit are shown in FIG. 11 enclosed within spaces 216 and 217 whose perimeter and boundary is determined by the dashed lines. The kit could be provided pre-sterilized and ready for connection to a patient 14 and hemofilter 182. Preferably, the kit includes two separate components which could be packaged together. The first component, contained in space 216, comprises an arterial line for connecting the patient 14 to the inlet of hemofilter 182. Preferably, arterial line component 216 includes a patient connector 218, sterile blood tubing 12, drip chamber 227, and a region of tubing 225 designed and constructed to be used with peristaltic pump (not shown). Arterial line component 216 also includes a connector 219 for connection to hemofilter 182. The second component of the kit, contained in space 217, includes container 160, filter unit 223, infusate conduit 192 which is connected to a blood return conduit 28, and an ultrafiltrate conduit 198. Valves 206, 208 and 212 although within the space defined by 217 need not be supplied with the kit. Blood return conduit 28 includes a patient connector 220, for connecting to patient 14, a hemofilter connector 222 for connection to hemofilter 182 and, preferably, a drip chamber 228. Ultrafiltrate conduit 198 includes a hemofilter connector 221 for connection to hemofilter 182 and, preferably, a region of tubing 226 designed and constructed to be used with a peristaltic pump (not shown). Additionally, a kit similar to the one just described could be provided for use with hemofiltration system 180 shown in FIGS. 6–8. In such a kit (not shown) filter unit 223 would be replaced by a conduit 190 connectable to the sterile side 186 of hemofilter 182 (see FIG. 6).

Components suitable for use in the various arrangements of the invention are known and readily available to those of ordinary skill in the art. For example, membranes can be made from polyvinyl alcohol, cellulose acetate, and the like, optionally including an anti-blood-clotting agent such as heparin. Tubes and other connections can be made of medical-grade polymer, stainless steel, or the like. Those skilled in the art would readily appreciate that the embodiments described herein and parameters or materials listed herein are meant to be exemplary and that actual arrangements, materials, and parameters will depend upon the specific application and conditions for which the methods and apparatus of the present invention are used. It is, therefore, to be understood that the foregoing embodiments are presented by way of example only and that, within the scope of the appended claims and equivalents thereto, the invention may be practiced otherwise than as specifically described.

What is claimed is:

1. A system for processing blood from an individual comprising
    a draw path coupled to the individual to convey blood from the individual, a blood treatment unit communicating with the draw path comprising a hemofiltration membrane operating to remove waste fluid comprising water and at least one ionic species from the blood, a waste outlet operating to convey the waste fluid from the blood treatment unit, and a treated blood outlet operating to convey treated blood from the blood treatment unit following removal of the waste fluid, a non-sterile source of at least one replacement ionic species, a replacement fluid generation assembly comprising a waste treatment unit coupled to the waste outlet operating to remove ionic species from the waste fluid to create essentially pure sterile water, and a pure water outlet operating to convey the essentially pure sterile water from the waste treatment unit, and a replenishment unit coupled to the pure water outlet and the non-sterile source and including a semipermeable membrane to convey by ionic transport the at least one replacement ionic species from the non-sterile source into the essentially pure sterile water to form an essential sterile replacement fluid, and a replacement fluid outlet operating to convey the essentially sterile replacement fluid from the replenishment unit, and a return path coupled to the individual and communicating with the treated blood outlet and the replenishment fluid outlet to convey treated blood and the essentially sterile replacement fluid to the individual.

2. A system for processing blood from an individual comprising a draw path coupled to the individual to convey blood from the individual, a blood treatment unit communicating with the draw path comprising a hemofiltration membrane operating to remove waste fluid comprising water and at least one ionic species from the blood, a waste outlet operating to convey the waste fluid from the blood treatment unit, and a treated blood outlet operating to convey treated blood from the blood treatment unit following removal of the waste fluid, a sterile source of at least one replacement ionic species, a replacement fluid generation assembly comprising a waste treatment unit coupled to the waste outlet operating to remove ionic species from the waste fluid to create essentially pure sterile water, and a pure water outlet operating to convey the essentially pure sterile water from the waste treatment unit, and a replenishment unit coupled to the pure water outlet and the sterile source and including a semipermeable membrane to convey by ionic transport the at least one replacement ionic species from the sterile source into the essentially pure sterile water to form an essential sterile replacement fluid, and a replacement fluid outlet operating to convey the essentially sterile replacement fluid from the replenishment unit, and a return path coupled to the individual and communicating with the treated blood outlet and the replenishment fluid outlet to convey treated blood and the essentially sterile replacement fluid to the individual.

3. A system according to claim 1 or 2 wherein the waste treatment unit includes a reverse osmosis membrane.

* * * * *

UNITED STATES PATENT AND TRADEMARK OFFICE
CERTIFICATE OF CORRECTION

PATENT NO. : 6,582,385 B2
DATED : June 24, 2003
INVENTOR(S) : Jeffrey H. Burbank et al.

It is certified that error appears in the above-identified patent and that said Letters Patent is hereby corrected as shown below:

Title page,
Item [73], the name of the Assignee, should read -- NxStage Medical, Inc. --

Signed and Sealed this

Fourteenth Day of October, 2003

JAMES E. ROGAN
*Director of the United States Patent and Trademark Office*